United States Patent
Hagihara

(10) Patent No.: US 11,633,085 B2
(45) Date of Patent: Apr. 25, 2023

(54) CHARGING DEVICE

(71) Applicant: Sony Olympus Medical Solutions Inc., Tokyo (JP)

(72) Inventor: Masahiro Hagihara, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 104 days.

(21) Appl. No.: 16/799,832

(22) Filed: Feb. 25, 2020

(65) Prior Publication Data

US 2020/0305684 A1 Oct. 1, 2020

(30) Foreign Application Priority Data

Mar. 25, 2019 (JP) .............................. JP2019-056724

(51) Int. Cl.
*A61B 1/00* (2006.01)
*H02J 7/00* (2006.01)
*A61B 1/04* (2006.01)
*H02J 50/12* (2016.01)

(52) U.S. Cl.
CPC ...... *A61B 1/00034* (2013.01); *A61B 1/00029* (2013.01); *A61B 1/00105* (2013.01); *A61B 1/00114* (2013.01); *A61B 1/042* (2013.01); *H02J 7/0045* (2013.01); *H02J 50/12* (2016.02)

(58) Field of Classification Search
CPC ............ A61B 1/00034; A61B 1/00029; A61B 1/00105; A61B 1/00114; A61B 1/042; A61B 1/00016; A61B 1/0669; H02J 7/0045; H02J 50/12; H02J 7/0044; H02J 50/10

See application file for complete search history.

(56) References Cited

U.S. PATENT DOCUMENTS

| | | | | |
|---|---|---|---|---|
| 9,370,296 B2* | 6/2016 | He | ...................... | A61B 1/00131 |
| 2006/0028169 A1* | 2/2006 | Winn | ..................... | H02J 7/0044 |
| | | | | 320/107 |
| 2008/0129251 A1* | 6/2008 | Lam | ...................... | H02J 7/0045 |
| | | | | 320/149 |
| 2008/0139881 A1* | 6/2008 | Cover | ................. | A61B 1/00105 |
| | | | | 600/103 |
| 2010/0315036 A1* | 12/2010 | Liao | ...................... | H02J 7/0042 |
| | | | | 320/107 |
| 2011/0022748 A1* | 1/2011 | Edwards | ............. | G06F 13/4221 |
| | | | | 710/63 |
| 2011/0193948 A1* | 8/2011 | Amling | .............. | A61B 1/00059 |
| | | | | 348/68 |
| 2012/0235641 A1* | 9/2012 | Yang | ..................... | H02J 7/0068 |
| | | | | 320/110 |
| 2013/0137939 A1* | 5/2013 | He | ......................... | A61B 50/20 |
| | | | | 600/301 |

(Continued)

FOREIGN PATENT DOCUMENTS

| JP | 2000287987 A | 10/2000 |
|---|---|---|
| JP | 2002291691 A | 10/2002 |

(Continued)

*Primary Examiner* — Anh Tuan T Nguyen
*Assistant Examiner* — Shankar Raj Ghimire
(74) *Attorney, Agent, or Firm* — Xsensus LLP

(57) ABSTRACT

A charging device includes: a holder detachably connected to a connector of a camera head to which an endoscope is detachably connected; and a power supplier configured to supply power to a battery of the camera head held by the holder.

10 Claims, 4 Drawing Sheets

(56) References Cited

U.S. PATENT DOCUMENTS

2014/0184771 A1* 7/2014 Mazzetti .................. H02J 5/00
                                                                    348/75
2017/0332888 A1* 11/2017 Amling .............. H04N 5/23241
2018/0008304 A1* 1/2018 Nakamura .......... A61B 1/00032
2020/0107710 A1* 4/2020 Duckett, III ......... G02B 27/283

FOREIGN PATENT DOCUMENTS

| JP | 2005-348941 A | | 12/2005 |
|----|---------------|---|---------|
| JP | 2005348941 A | * | 12/2005 |
| JP | 2010509990 A | | 4/2010 |
| JP | 2012055697 A | | 3/2012 |
| JP | 2013054234 A | | 3/2013 |
| JP | 2013544144 A | | 12/2013 |
| JP | 5678027 B2 | | 2/2015 |
| JP | 2018000753 A | | 1/2018 |
| WO | WO-2018230068 A1 | | 12/2018 |

* cited by examiner

CHARGING DEVICE

This application claims priority from Japanese Application No. 2019-056724, filed on Mar. 25, 2019, the contents of which are incorporated by reference herein in its entirety.

BACKGROUND

The present disclosure relates to a charging device.

In the medical and industrial fields, endoscope devices for observation are widely used in subjects such as persons and mechanical structures. In general, such an endoscope is connected to an information processing device by a cable to transmit a video signal, power, or the like and handling of the cable or the like is a handler's stress. Used for this to be addressed is a wireless endoscope that does not use a cable interconnecting an endoscope and an information processing device.

The wireless endoscope incorporates a battery in place of a power line in a cable. After the battery is charged, the endoscope is sterilized at a high temperature and used for an operation or the like.

A sterilization tray, a carrying device, and the like have been proposed as a wireless endoscope charging device (see, for example, JP 2005-348941 A and JP 5678027 B2).

SUMMARY

The sterilization tray and the carrying device in JP 2005-348941 A and JP 5678027 B2 are intended for specific surgical instruments. Accordingly, especially in a case where camera heads of a wireless endoscope are targets, a dedicated tray or a carrying device is required for each of the camera heads of the wireless endoscope, which have various shapes depending on the medical treatment target and application. This requirement leads to the problem of low versatility.

According to one aspect of the present disclosure, there is provided a charging device including: a holder detachably connected to a connector of a camera head to which an endoscope is detachably connected; and a power supplier configured to supply power to a battery of the camera head held by the holder.

DETAILED DESCRIPTION

Figure 1:
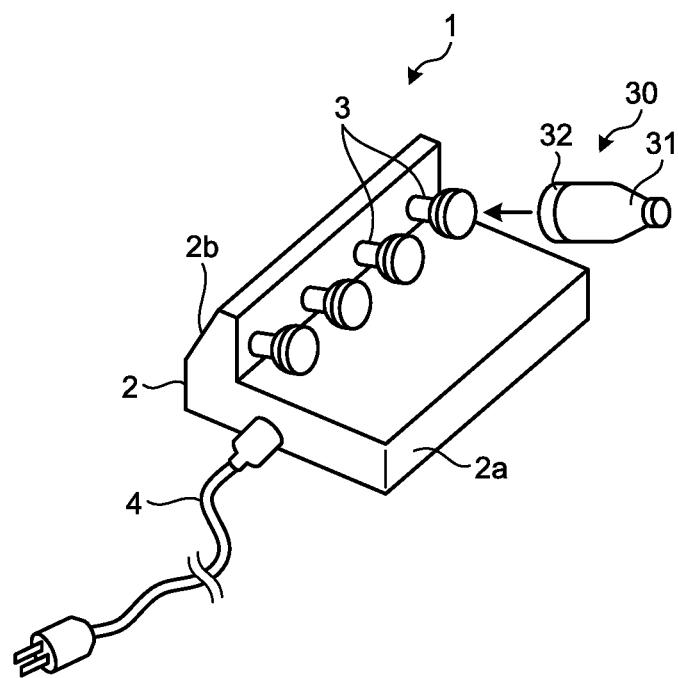
FIG. 1 is a diagram illustrating a schematic configuration of a charging device of a camera head of a wireless endoscope according to a first embodiment.

Hereinafter, embodiments for implementing the present disclosure (hereinafter, embodiments) will be described with reference to the drawings. The present disclosure is not limited by the embodiments described below. Further, in the description of the drawings, the same parts are denoted by the same reference numerals.

First Embodiment

Figure 2:
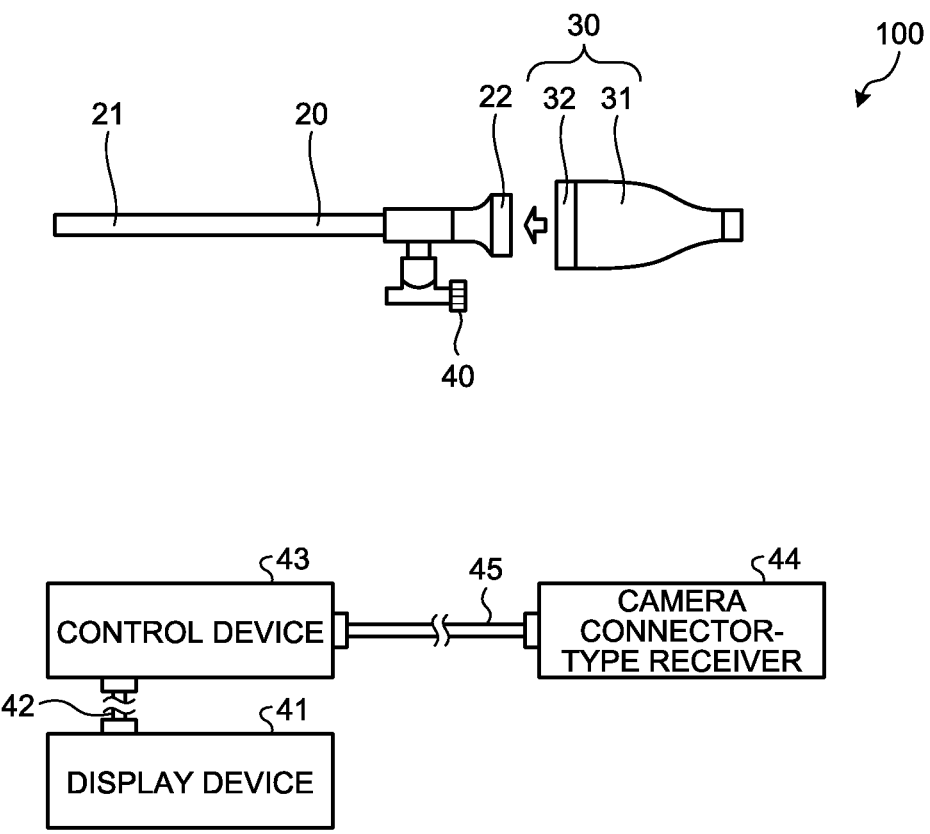
FIG. 2 is a schematic configuration diagram of an endoscope device.
Figure 3:
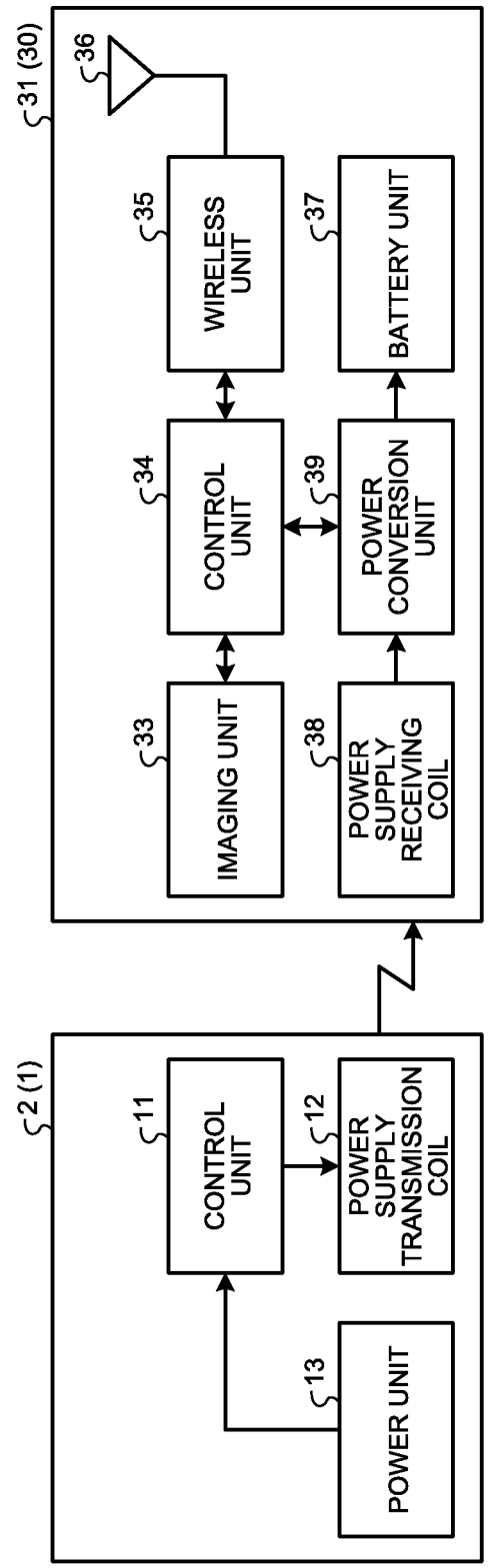
FIG. 3 is a block diagram of the camera head and the charging device.

FIG. 1 is a diagram illustrating a schematic configuration of a charging device 1 of a camera head 30 of an endoscope 20 according to a first embodiment. FIG. 2 is a schematic configuration diagram of an endoscope device 100. FIG. 3 is a block diagram of the camera head 30 and the charging device 1.

The charging device 1 is provided with a main body unit 2 having an air-tight or liquid-tight inner portion, a holding unit 3 detachable from an endoscope connection portion 32 of the camera head 30 of the endoscope 20, a power supply transmission coil 12 supplying power to a battery unit 37 of the camera head 30 held by the holding unit 3, and a power cable 4.

The main body unit 2 has a first main body unit 2a having a flat surface portion placed on a table or the like and a second main body unit 2b standing from an end portion of the first main body unit 2a. A plurality of the holding units 3 detachable from the endoscope connection portion 32 of the camera head 30 are provided on the side surface of the second main body unit 2b that is on the side where the first main body unit 2a extends. Although one holding unit 3 may be provided in place of the plurality of holding units 3, the number of the holding units 3 is preferably two or more from the viewpoint of power supply efficiency. The main body unit 2 is configured such that the inner portion is air-tight or liquid-tight so that disinfection or sterilization is possible in a state where the camera head 30 is mounted. In addition, the casing of the main body unit 2 is also made of a material resistant to disinfection and sterilization.

In addition, as illustrated in FIG. 3, the main body unit 2 has a control unit 11, the power supply transmission coil 12, and a power unit 13. The power unit 13 is supplied with power from an external outlet or the like by, for example, the power cable 4 and supplies power to each circuit in the charging device 1. When the connection portion 32 of the camera head 30 is connected to the holding unit 3 and the power cable 4 is connected to the external outlet or the like, an electric current flows through the power supply transmission coil 12 under the control of the control unit 11. The power supply transmission coil 12 generates a magnetic flux by the electric current flowing. As a result, a magnetic flux is also generated in a power supply receiving coil 38 (described later) in the camera head 30 and an electric current also flows through the power supply receiving coil 38. A power conversion unit 39 converts the electric current generated in the power supply receiving coil 38 into electric energy and supplies power to the battery unit 37. Although the wireless power supply in the first embodiment is described as an electromagnetic induction method, the present disclosure is not limited thereto and the wireless power supply may be an electromagnetic resonance method or a radio wave method. In addition, although the power supply method of the charging device 1 is not limited to wireless and may be wired power supply, the wireless power supply is preferable for the electrical safety, sealability, or the like at a time when sterilization or the like is performed during charging by means of the charging device 1.

The power supply transmission coil 12 is preferably disposed for each camera main body unit near camera main body units 31 connected to the holding units 3. It is possible to perform charging in a stable and efficient manner by disposing the power supply transmission coil 12 for each camera main body unit near the camera main body units 31. The power supply transmission coil 12 may be provided in, for example, the first main body unit 2a and below the camera main body unit 31 connected to the holding unit 3 or the second main body unit 2b and beside the camera main body unit 31 connected to the holding unit 3. From the viewpoint of shortening the distance between the camera main body unit 31 and the power supply transmission coil 12 and improving charging efficiency, it is preferable that the power supply transmission coil 12 is provided in each holding unit 3.

As illustrated in FIG. 2, the wireless endoscope device 100 is provided with the endoscope 20, the camera head 30, a light source device 40, a display device 41, a first transmission cable 42, a control device 43, a receiver 44, and a second transmission cable 45.

A rigid endoscope constitutes the endoscope 20. In other words, the endoscope 20, which is inserted into a living body, has an elongated shape in which the endoscope 20 as a whole is hard or a part of the endoscope 20 is soft and the other part of the endoscope 20 is hard. The endoscope 20 is provided with an insertion portion 21 and an eyepiece unit 22. The insertion portion 21 is a linearly extending part inserted into a living body. An objective optical system configured by means of one or a plurality of lenses and capturing light emitted from a subject and a transmission optical system (not illustrated) transmitting the light to the eyepiece unit 22 are provided in the insertion portion 21. The eyepiece unit 22 is provided at the proximal end of the insertion portion 21, incorporates an eyepiece optical system (not illustrated) emitting light transmitted from the insertion portion 21, and is detachably connected to the connection portion 32 of the camera head 30.

The light source device 40 is detachably connected to the endoscope 20 and supplies illumination light to the endoscope 20. The illumination light supplied to the endoscope 20 is emitted from the distal end of the endoscope 20 into the living body. The light (subject image light) emitted into the living body and reflected in the living body is condensed by the objective optical system in the insertion portion 21.

The camera head 30 is provided with the camera main body unit 31 in which an imaging unit 33 or the like is stored in an air-tight or liquid-tight manner and the connection portion 32 detachably connected to the endoscope 20. The camera main body unit 31 captures a subject image condensed by the endoscope 20 under the control of a control unit 34 and outputs an imaging signal obtained by the imaging.

As illustrated in FIG. 3, the camera main body unit 31 has the imaging unit 33, the control unit 34, a wireless unit 35, an antenna unit 36, the battery unit 37, the power supply receiving coil 38, and the power conversion unit 39.

The control unit 34 outputs the imaging signal captured by the imaging unit 33 to the wireless unit 35 and wirelessly transmits the imaging signal to the receiver 44 via the antenna unit 36. At this time, the control unit 34 may or may not convert the imaging signal into a signal form different from the form of output from the imaging unit 33. The receiver 44 supplies the received imaging signal to the control device 43 by means of the second transmission cable 45. The control device 43 generates an endoscope image signal from the imaging signal and outputs the endoscope image signal to the display device 41 by means of the first transmission cable.

In a case where the camera head 30 is charged after the wireless endoscope device 100 is used, the charging may be performed by the camera head 30 connected to the eyepiece unit 22 of the endoscope 20 being detached and the connection portion 32 for the endoscope 20 of the detached camera head 30 being connected to the holding unit 3 of the charging device 1. The charging device 1 of the first embodiment has the holding unit 3 that may be connected to the connection portion 32 of the camera head 30. Although the endoscope 20 and the camera head 30 have various shapes depending on medical department characteristics or for grip to be ensured, the eyepiece unit 22 and the connection portion 32 are unified in shape in order to enable combinations with different endoscopes 20 and camera heads 30. Accordingly, charging may be performed regardless of the type of the camera head and regardless of the shape of the camera main body unit 31. Accordingly, a dedicated tray or a carrying device is not required even for various camera heads having different shapes.

Figure 4:
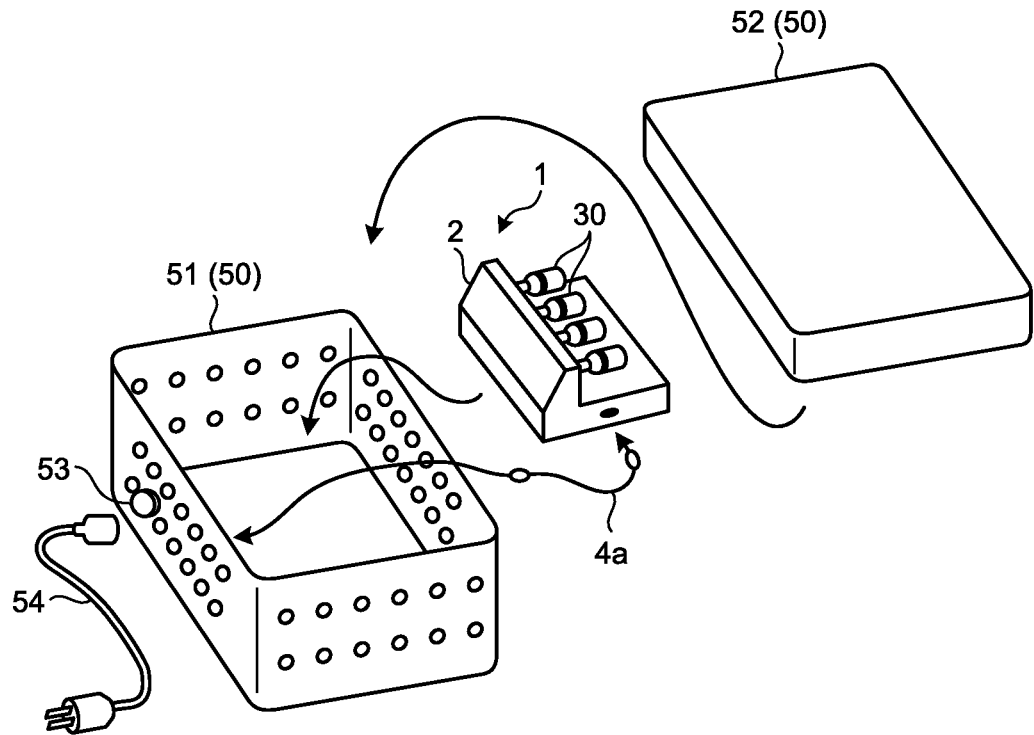
FIG. 4 is a diagram illustrating camera head sterilization.

In addition, a sterilization container 50 illustrated in FIG. 4 or the like may be used in the case of performing subsequent to charging and sterilization. FIG. 4 is a diagram illustrating the sterilization of the camera head 30.

The sterilization container 50 has a main body unit 51 and a lid portion 52. The main body unit 51 is provided with a connector 53 to which a power cable 54 is connected. The connector 53 is an air-tight through terminal (hermetic terminal).

The charging device 1 to which the camera main body unit 31 is connected is stored in the main body unit 51 of the sterilization container 50 and the charging device 1 and the connector 53 inside the sterilization container 50 are interconnected by means of a cable 4a. After the charging device 1 is stored in the main body unit 51, the main body unit 51 is covered with the lid portion 52 and put into an autoclave in a state of being wrapped with a sterile cloth (not illustrated). At this time, only the periphery of the connector 53 is not covered with the sterile cloth. It is possible to perform charging while maintaining sterilization by connecting the power cable 54 to an outlet after the sterilization.

Although the second main body unit standing from the flat plate-shaped first main body unit 2a is provided with the holding unit 3 in the first embodiment, the present disclosure is not limited thereto. For example, the holding unit 3 may stand from the flat plate-shaped main body unit without the second main body unit 2b being provided. Further, wireless power supply may be performed with the charging device 1 provided with a battery although the charging device 1 supplies power from an external commercial power supply.

In addition, although the control device 43 and the receiver 44 are separately provided in the first embodiment, the receiver 44 may be provided in the control device 43.

Second Embodiment

Figure 5:
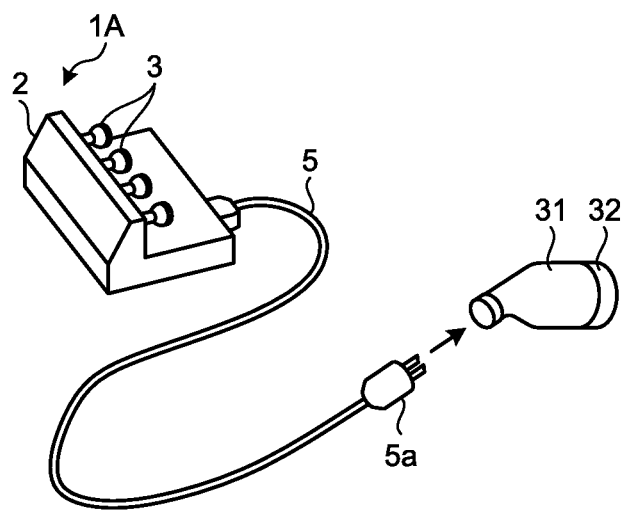
FIG. 5 is a diagram illustrating a schematic configuration of a charging device according to a second embodiment.

FIG. 5 is a diagram illustrating a schematic configuration of a charging device 1A according to a second embodiment. The power cable 4 is not illustrated in FIG. 5.

The charging device 1A has a wired power cable 5 for emergency power supply. A plug 5a of the sterilizable wired power cable 5 is detachable from a connector provided on the camera head 30. The plug 5a is provided in the end portion of the wired power cable 5 opposite to the end portion of the wired power cable 5 that is connected to the charging device 1A.

The camera head 30 captures an optical subject image transmitted by the endoscope 20 and outputs an imaging signal obtained by the imaging to the control device 43 via the wireless unit 35, the antenna unit 36, the receiver 44, and the second transmission cable 45. In the second embodiment, the wired power cable 5 is connected to the connector of the camera head. As a result, wired power supply to the camera head 30 may be performed even in a case where the battery of the camera head 30 runs out during the output and it is possible to perform imaging signal output to the control device 43.

The charging device 1A may have a built-in antenna receiving the imaging signal output from the camera head 30.

The charging device has the effect that a dedicated tray or a carrying device is not required even for various camera heads having different shapes.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A charging system for use with a first camera head having a connector and a first endoscope having an eyepiece, the charging system comprising:
    a holder configured to be detachably connected to physically mate with and electrically connect with the connector of the first camera head, the connector of the first camera head being configured to be detachably connected to physically mate with the eyepiece of the first endoscope, wherein the connector of the first camera head is detached from the eyepiece of the first endoscope when connected to the holder and wherein the connector is configured such that the holder or the eyepiece physically mates with the same facing surface of the connector; and
    a power supplier configured to supply power to a battery of the first camera head held by the holder.

2. The charging system according to claim 1, wherein the power supplier is configured to supply power supply wirelessly to the first camera head.

3. The charging system according to claim 1, wherein the power supplier is disposed near the holder.

4. The charging system according to claim 1, wherein the power supplier comprises a coil and is disposed in the holder.

5. The charging system according to claim 1, wherein the holder is configured to be detachably connected to a connector of a second camera head to which an eyepiece of a second endoscope is to be detachably connected.

6. The charging system according to claim 1, comprising
    a main body air-tight body or water-tight body, the main body being provided with the holder and being the power supplier.

7. The charging system according to claim 2, further comprising
    a wired power cable having a first end portion connected to the charging system and a second end portion, opposite to the first end portion, that includes a plug detachable from the connector of the first camera head and configured to supply power to the first camera head.

8. The charging system according to claim 1, wherein the holder is a first holder, and
    the charging system further comprises a second holder configured to be detachably connected to a connector of a second camera head to which an eyepiece of a second endoscope is detachably connected.

9. The charging system according to claim 8, wherein a shape of the first holder is same as a shape of the second holder.

10. The charging system according to claim 1, wherein the holder is configured to be detachably connected to the connector of the first camera head in a same manner as the eyepiece of the first endoscope is to be detachably connected to the connector of the first camera head.

* * * * *